(12) United States Patent
Johnson

(10) Patent No.: US 8,047,842 B2
(45) Date of Patent: Nov. 1, 2011

(54) RECIPROCAL REVERSE ROTATION ENDODONTIC FILE

(76) Inventor: William B. Johnson, Tulsa, OK (US)

(*) Notice: Subject to any disclaimer, the term of this patent is extended or adjusted under 35 U.S.C. 154(b) by 294 days.

(21) Appl. No.: 12/193,411

(22) Filed: Aug. 18, 2008

(65) Prior Publication Data

US 2010/0040994 A1   Feb. 18, 2010

(51) Int. Cl.
*A61C 1/02* (2006.01)
(52) U.S. Cl. .................... 433/102; 206/369
(58) Field of Classification Search ............ 433/102, 433/72, 75; 206/368, 369, 63.5
See application file for complete search history.

(56) References Cited

U.S. PATENT DOCUMENTS

| | | | | |
|---|---|---|---|---|
| 3,366,230 A | * | 1/1968 | Loran | 206/63.5 |
| 3,772,791 A | * | 11/1973 | Malmin | 433/224 |
| 4,602,900 A | * | 7/1986 | Arpaio et al. | 408/230 |
| 5,653,590 A | * | 8/1997 | Heath et al. | 433/102 |
| 5,882,198 A | * | 3/1999 | Taylor et al. | 433/102 |
| 5,975,899 A | * | 11/1999 | Badoz et al. | 433/102 |
| 6,267,592 B1 | * | 7/2001 | Mays | 433/102 |
| 6,293,795 B1 | | 9/2001 | Johnson | |
| 6,299,445 B1 | * | 10/2001 | Garman | 433/102 |
| 6,419,488 B1 | * | 7/2002 | McSpadden et al. | 433/102 |
| 6,942,484 B2 | * | 9/2005 | Scianamblo | 433/102 |
| 2001/0034005 A1 | * | 10/2001 | Matsutani et al. | 433/102 |
| 2007/0031783 A1 | * | 2/2007 | Cantatore et al. | 433/102 |

FOREIGN PATENT DOCUMENTS

| EP | 1184004 A | 3/2002 |
|---|---|---|
| EP | 1752109 A | 2/2007 |

OTHER PUBLICATIONS

Extended European Search Report issued by the European Patent Office, Munich, Germany, dated Dec. 1, 2009 (6 pages).

* cited by examiner

*Primary Examiner* — John J Wilson
(74) *Attorney, Agent, or Firm* — Gable Gotwals

(57) ABSTRACT

A single use, reciprocal reverse rotation, endodontic file includes a plurality of spaced apart helical flutes with spiraled lands therebetween. The lands have an edge with a positive cutting angle when the file is rotated in one direction and a scraping angle when rotated in the opposite direction. The file provides for sequential rotation of a selected angle in a forward direction followed by rotation of a slightly less angle in a reverse direction. In one embodiment, the cross-sectional area of the flutes is concave polygonal-shaped at a proximal end of the file and square-shaped at the distal end. In another embodiment, the cross-sectional area of the flutes is convex arcuate-shaped, the lands lying normal to the central longitudinal axis of the file. The handle portion of the file may be configured for use in a rotary handpiece or for manual rotation.

6 Claims, 4 Drawing Sheets

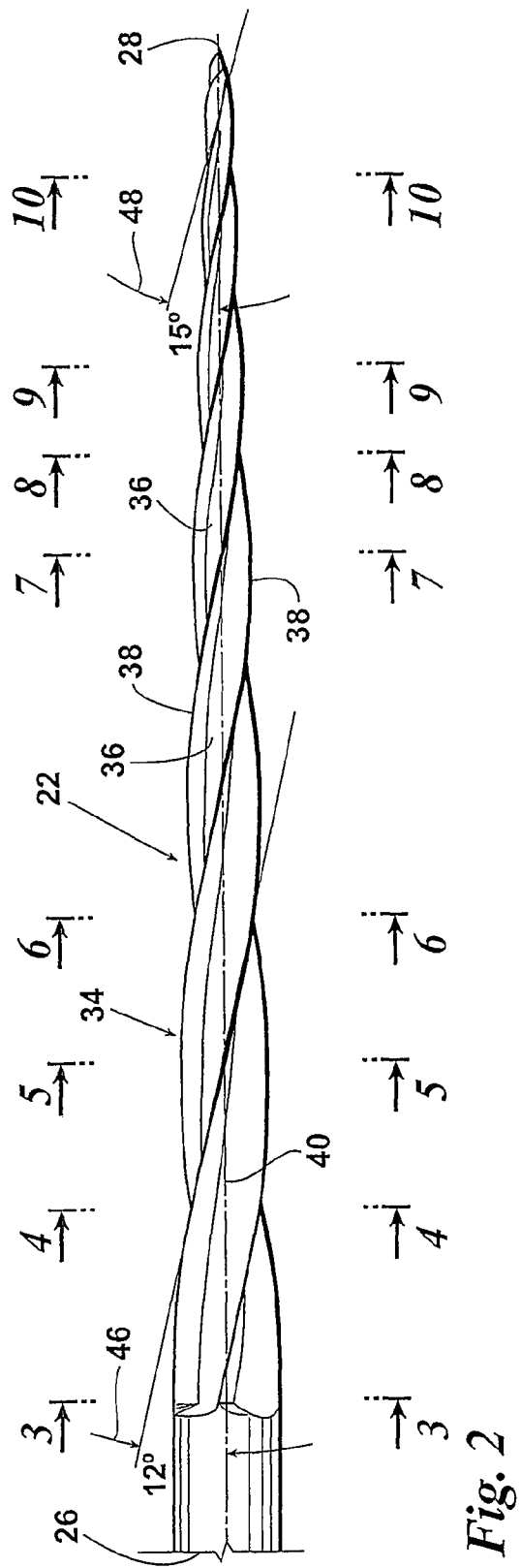

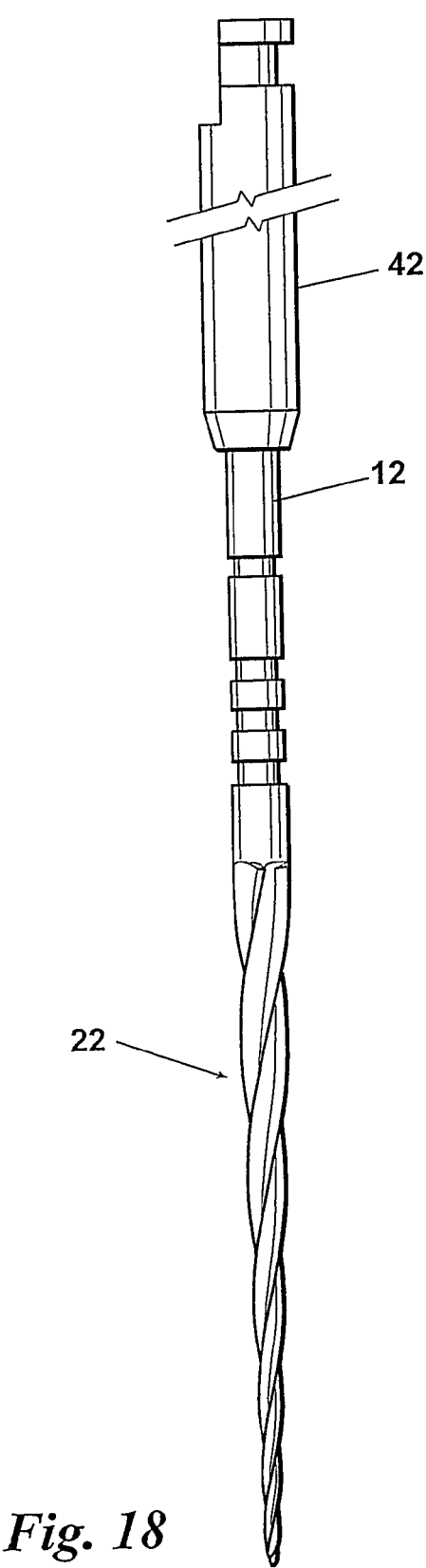
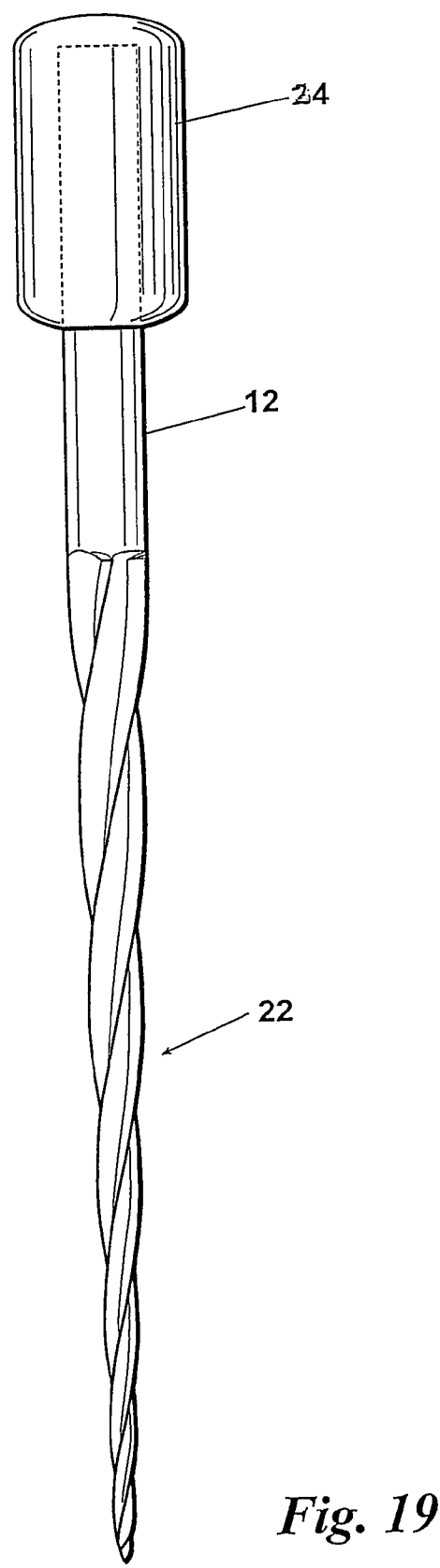
*Fig. 18*
*Fig. 19*

RECIPROCAL REVERSE ROTATION ENDODONTIC FILE

REFERENCE TO PENDING APPLICATIONS

This application is not based upon any pending domestic or international patent applications.

REFERENCE TO MICROFICHE APPENDIX

This application is not referenced in any microfiche appendix.

BACKGROUND OF THE INVENTION

1. Field of the Invention

This invention relates generally to the field of dentistry and more particularly to endodontic instruments used for cleaning and enlarging a root canal of a tooth. The files of this invention are particularly well-suited for rotation first in one direction through a given arc and then rotation in a reverse direction through a reduced arc.

2. Description of the Related Art

A key procedure in endodontic therapy of treating an infected tooth is cleaning and enlarging the root canal of the tooth prior to filling with an inert obturating material such as gutta percha. Successful removal of infected tissue from the tooth greatly improves the likelihood that a patient will retain the tooth. Two alternate, primary methods have been used in cleaning and enlarging the root canal: step-back preparation and crown-down preparation. Both methods require substantial skill and time to perform properly, and each generally employs a series of three to five endodontic files that are manually rotated and advanced into the canal to clean canal surfaces and eject the debridement material from the canal for removal. Step-back preparation first employs a small instrument to the apex of the canal and then employs larger instruments for enlargement of the apex. Additional larger instruments are then applied slightly short of the apex to back out of the canal and create a taper. Crown-down preparation first employs a large instrument at the orifice of the canal. The instrument is worked apically until reaching resistance. Smaller instruments are then applied in proceeding down the canal.

Employing a handpiece to mechanically duplicate the hand techniques associated with these methods, including rotating a file, provides a beneficial improvement in efficiency. In the past, this efficiency improvement would often come at the expense of the clinician losing tactile feedback and, therefore, control of the procedure. Although the rotary handpiece has been greatly improved—see my U.S. Pat. No. 6,293,795—rotary files have not kept pace with changes in clinical practice.

Clinicians are increasingly being encourages to employ instruments as single use for safety and health reasons, however endodontic instruments are commonly employed in packages in four or more of a single size. In contrast, in a single use system the clinician first selects a small exploring file to establish a guide path to the apex and determine a working length of the canal. The clinician then selects a single working file having the desired apical size and taper to prepare the entire canal from orifice to apex. Thus a single use system can employ a package of two or three instruments, that is, an exploring file and one or two working files, all of which are used for only one patient and then the instruments are discarded.

BRIEF SUMMARY OF THE INVENTION

An endodontic file that is well-suited for rotation first in one direction through a given arc and then rotation in a reverse direction through a reduced arc includes an elongated tapered metal file having a proximal end, a distal end, a handle portion, and "n" spaced apart helical flutes with spiraled lands therebetween. The distal end is dimensioned and configured for a selected finished root canal apex and the taper is configured to provide a desired finished root canal configuration. The helix angle of the flutes increases toward the distal end and is preferably at least 3° greater at the distal end than at the proximal end. Each of the lands has an edge that has a positive cutting angle when the file is rotated in one direction and a scraping angle when the file is rotated in the opposite direction. The handle portion may be configured for manual manipulation or for use in a rotary handpiece. Sequential forward and rearward rotation of the file by the handpiece may include rotation of only slightly more than 90° in opposite directions.

In a preferred embodiment, the edge cuts into a surface of a root canal when the file is rotated in the forward direction and scrapes the surface of the root canal when the file is rotated in the rearward direction. The rotation in the forward direction passes through a minimum angle of about 90° and the immediately following rotation in the rearward direction passes through an angle less than the angle of rotation in the forward direction. In another preferred embodiment, the cross-sectional area of the flutes is concave polygonal-shaped at the proximal end and gradually becomes square-shaped at the distal end. In yet another embodiment, the cross-sectional area of the flutes is convex arcuate-shaped with the lands therebetween lying normal to the central longitudinal axis of said file.

The file of this invention may be part of a package that includes a scouting file for use in determining a glide path to an apex of a root canal and a working length of the root canal. The file may also form part of a sterilized pre-packaged two or three file system for one time use to prepare the root canal.

A better understanding of the invention will be obtained from the following detailed description of the preferred embodiments and claims, taken in conjunction with the attached drawings.

BRIEF DESCRIPTION OF THE DRAWINGS

FIG. 2 is a view of an endodontic file configured for use by sequential rotation in the forward direction followed by rotation in the rearward direction. The file has at least three spaced apart helical flutes with lands therebetween, each land having a spiraled scraping/cutting edge that, when the file is rotated in one direction, has a positive cutting angle and, when rotated in the opposite direction, has a scraping angle.

FIG. 3 is a cross-sectional view of the file taken along section line 3-3 of FIG. 2.

FIG. 4 is a cross-sectional view of the file taken along section line 4-4 of FIG. 2.

FIG. 5 is a cross-sectional view of the file taken along section line 5-5 of FIG. 2.

FIG. 6 is a cross-sectional view of the file taken along section line 6-6 of FIG. 2.

FIG. 7 is a cross-sectional view of the file taken along section line 7-7 of FIG. 2.

FIG. 8 is a cross-sectional view of the file taken along section line 8-8 of FIG. 2.

FIG. 9 is a cross-sectional view of the file taken along section line 9-9 of FIG. 2.

FIG. 10 is a cross-sectional view of the file taken along section line 10-10 of FIG. 2.

FIG. 18 is a view of a file configured for manual manipulation.

FIG. 19 is a view of a file configured for use in a rotary chuck.

DETAILED DESCRIPTION OF THE PREFERRED EMBODIMENTS

Figures 1, 11, 12:
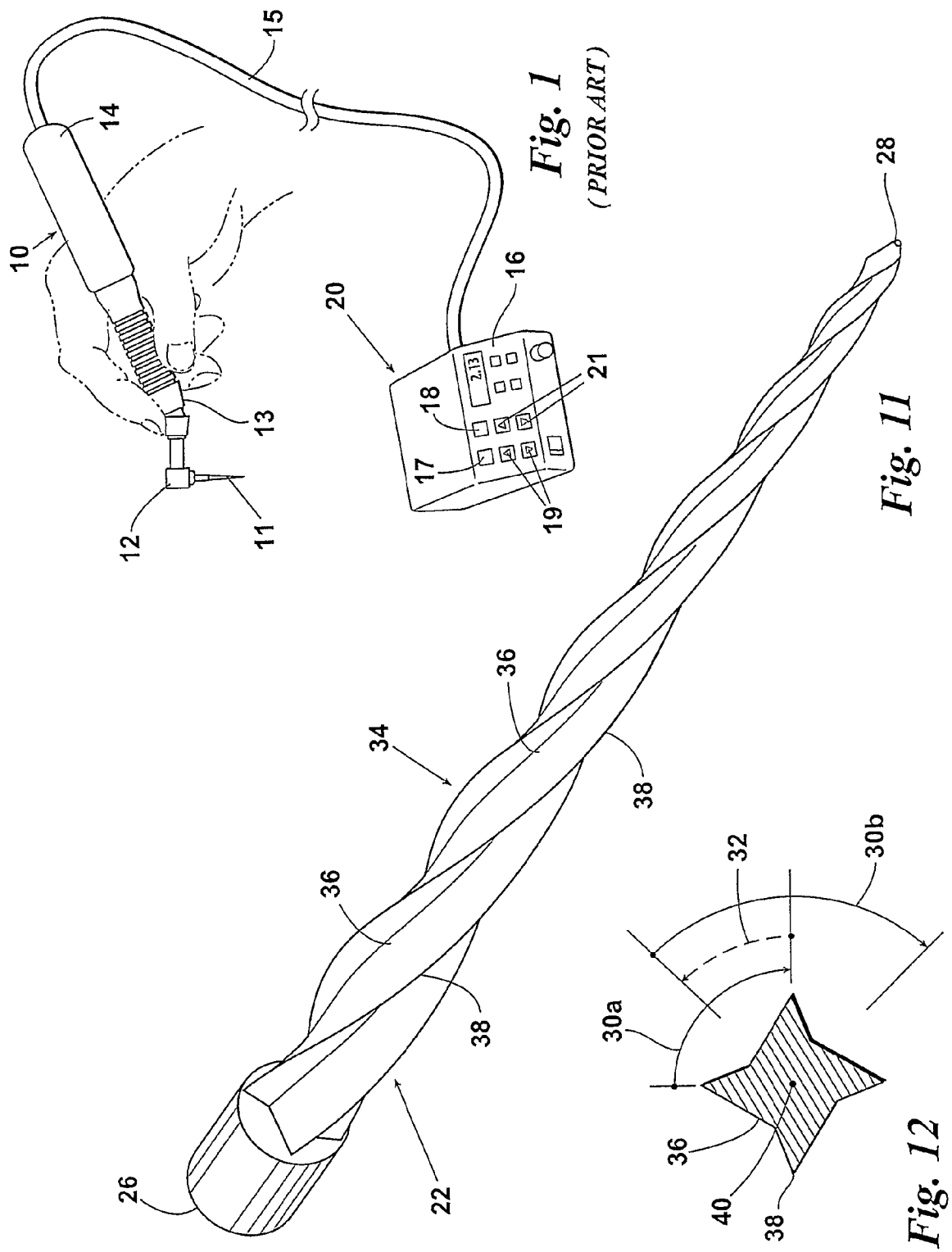
FIG. 1 is a view of a prior art of a dental handpiece and portions of its control system.
FIG. 11 is an isometric view of a file showing cross-sectional areas of the flutes along the tapered portion of the file.
FIG. 12 is a cross-sectional view of the file of FIG. 11 showing preferred first and second arcs of rotation.

Preferred embodiments of an endodontic file will now be described with reference to the drawings and the elements illustrated in the drawings and identified by the following numbers:

10 Handpiece
11 Endodontic instrument
12 Handpiece head
13 Contra angle
14 Electric motor
15 Control cable
16 Microprocessor
17 Control key
18 Forward-reverse key
19 Forward rotation key
20 Control system
21 Reverse rotation key
22 Endodontic instrument
24 Handle for manual rotation
26 Proximal end
28 Distal end
30 Forward rotation
32 Reverse rotation
34 Working portion
36 Flute
38 Land
40 Central longitudinal axis
42 Rotary handpiece chuck
44 Cutting edge Referring to the drawings and first to FIG. 1, a schematic representation of a prior art endodontic handpiece 10 and its control system 20 are shown. An endodontic instrument or file 11 is held securely in a chuck of a handpiece head 12 for rotation about its longitudinal axis. File 11 may be any endodontic instrument of useful design but preferably is a single use instrument system made according to the invention disclosed herein. Head 12 is an integral component of a conventional contra angle 13, providing a drive train and gears (not shown in detail) necessary to rotate file 11 at a desired rate of rotation. An electric motor 14 is fastened to contra angle 13, usually by way of complementary threaded body parts, and engages the drive train of contra angle 13 to rotate file 11. Motor 14 is connected by a control cable 15 to control system 20, which typically includes a microprocessor unit 16 (shown schematically in part). Microprocessor 16 is capable of electronically controlling and programming motor parameters such as speed, torque, and direction of rotation for a selected endodontic type file.

Microprocessor 16, including software (not shown), provides means for setting the regime or method of rotation of the endodontic file 11. A keyboard of microprocessor 16 typically includes a control key 17 and a "forward and reverse" key 18 to access setting a forward rotation key 19 and a reverse rotation key 21. Settings appear in a display. In addition, microprocessor 16 provides similar keys (not shown) allowing setting of the time between the forward and reverse motions.

Microprocessor 16 also provides input keys (not shown) for setting a maximum amount of torque to be applied to file 11 to avoid exceeding breaking stresses. The amount of maximum torque allowed is set with regard to the particular type of file employed. In operation, when an operator programs a particular torque setting, microprocessor 16 and motor 14 will respond electronically if file 11 exceeds the limit by stopping or changing the direction of rotation. The preferred regime of operation is that the forward rotation exceeds that of the reverse rotation such that file 11 rotates through a series of forward and reverse motions and completes a circle of rotation such that cleaning of the root canal proceeds by means of a series of cutting and ejecting of debris cycles.

Referring now to FIGS. 2 to 11, a file 22 uniquely configured as part of a single use instrument system for cleaning and shaping a tooth root canal includes an elongated tapered metal file portion 34 having a proximal end 26, a distal end 28, and at least three spaced apart helical flutes 36 with spiraled lands 38 therebetween. Distal end 28 is dimensioned and configured for a selected finished root canal apex and tapered portion 34 is configured to provide a desired finished root canal configuration. In a preferred embodiment, the helix angle of the flutes 36 changes along tapered portion 34 toward distal end 28 so that helix angle 48 is preferably at least 3° greater than helix angle 46. Each flute 36 is concave polygonal-shaped so that land 38 has an edge that has a positive cutting angle when file 22 is rotated in one direction and a scraping angle when file 22 is rotated in an opposite direction.

File 22 is preferably applied in a root canal procedure in the manner illustrated by FIG. 12. A forward rotation 30a of file 22 passes through a selected minimum angle, such as, by example, 90°, and the immediately following rearward rotation 32 passes through an angle less than the forward rotation 30a. Rearward rotation 32 is then immediately followed by a second forward rotation 30b that passes through the selected minimum angle. This forward and reverse rotation cycle continues with file 22 being advanced in a root canal (not shown).

Figure 13:
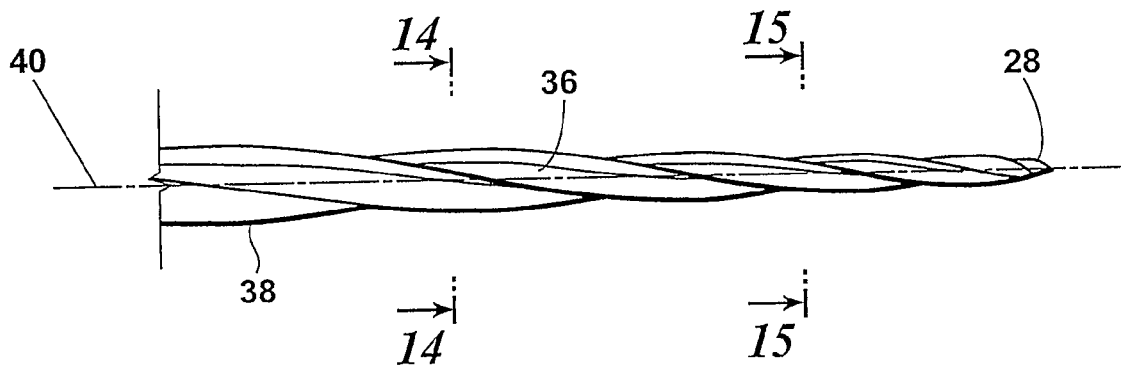
FIG. 13 is a partial view of another embodiment of an endodontic file configured for use by sequential rotation in the forward direction followed by rotation in the rearward direction.
Figure 14:
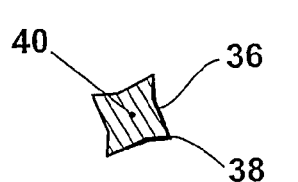
FIG. 14 is a cross-sectional view of the file taken along section line 14-14 of FIG. 13.
Figure 15:
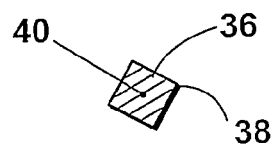
FIG. 15 is a cross-sectional view of the file taken along section line 15-15 of FIG. 13. The flutes are substantially square-shaped.

Referring now to FIGS. 13 to 15, in another preferred embodiment a cross-sectional area of the flutes 36 is concave polygonal-shaped at the proximal end 26 of an endodontic instrument 22 but gradually becomes square-shaped at distal end 28. In yet another preferred embodiment, a cross-sectional area of the flutes 36 is convex arcuate-shaped with a land 38 normal to longitudinal axis 40.

Figure 16:
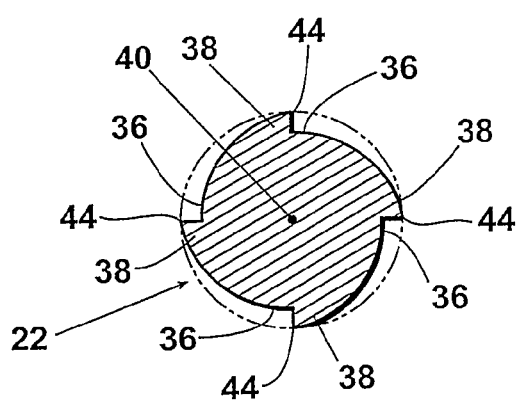
FIG. 16 is a cross-sectional view of another embodiment of an endodontic file configured for use by sequential rotation in the forward direction followed by rotation in the rearward direction. Rotation in the forward direction, that is clockwise in FIG. 16, provides positive cutting action while rotation in the counterclockwise direction provides only scraping action.
Figure 17:
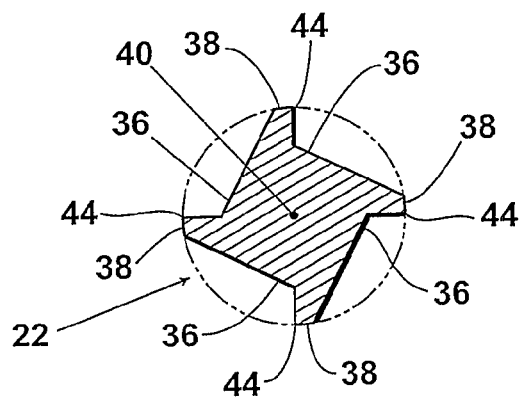
FIG. 17 is a cross-sectional view that shows an alternate design compared to FIG. 16.

FIG. 16 shows one preferred cross-sectional arrangement of an endodontic instrument 22. Each flute portion 36 provide a cutting edge 44 when the instrument is rotated clockwise about axis 40 but edge 44 becomes only a scraping edge when the file is rotated in the counterclockwise direction. The embodiment of FIG. 17 functions essentially like that of FIG. 16. The file has four cutting edges 44 formed by lands 38 that provide cutting edges when the instrument is rotated in the clockwise direction but form scraping edges when the file is rotated in the counterclockwise direction.

Referring now to FIG. 18, the file 22 has a handle portion 42 configured to be received in a handpiece 10 as seen in FIG. 1. In FIG. 19, the handle portion 24 of file 22 is configured for manual manipulation of instrument 22.

A file made according to this invention may be part of a sterilized pre-packaged system of files which includes a scouting file for use in determining a glide path to the apex of a root canal. The package may also include another file configured for coronal enlargement of the tooth root canal and still yet another file configured for apical enlargement of the tooth root canal.

While the preferred embodiments have been described with a certain degree of particularity, the phraseology and terminology employed were for purposes of description and not limitation. Many changes may be made in the details of construction and the arrangement of components without departing from the spirit and scope of this disclosure. An endodontic file according to this invention, therefore, is limited only by the scope of the attached claim or claims, including the full range of equivalency to which each element thereof is entitled.

What is claimed is:

1. An endodontic file for cleaning and shaping a tooth root canal comprising:
   an elongated tapered metal file having a proximal end, a distal end, a handle portion, and "n" spaced apart helical flutes with spiraled lands therebetween, a helix angle of said flutes increasing from said proximal end to said distal end;
   each of said lands having an edge that has a more positive cutting angle when the file is rotated in one direction and a scraping angle when the file is rotated in an opposite direction;
   said handle portion being configured for rotation in a handpiece, said handpiece selected from the group consisting of a manual handpiece and a rotary handpiece;
   said file being configured for sequential forwardly rotation followed by rearwardly rotation, thereby requiring rotation only slightly more than 360°/n forwardly then rearwardly to clean and shape a tooth root canal;
   a cross-sectional area of said flutes is concave polygonal-shaped at said proximal end and square-shaped at said distal end.

2. An instrument according to claim 1 wherein said edge cuts into a surface of a root canal when said file is rotated in the forward direction and scrapes the surface of the root canal when said file is rotated in the rearward direction.

3. An instrument according to claim 1 wherein the rotation in the forward direction passes through a minimum angle of about 90° and the immediately following rotation in the rearward direction passes through an angle less than said angle of rotation in the forward direction.

4. An instrument according to claim 1 further comprising said helix angle varies about 3° from said proximal end to said distal end.

5. An instrument according to claim 1 wherein said file is part of a package including a scouting file for use in determining a glide path to an apex of a root canal whereby a disposable package of endodontic instruments is provided for use in an endodontic procedure on a tooth and the instruments being thereafter discarded for sanitation benefits.

6. An instrument according to claim 5 forming a part of a sterilized pre-packaged system of one, two or three files for one time use to prepare the root canal.

* * * * *